United States Patent
Nowak et al.

(10) Patent No.: US 10,213,627 B2
(45) Date of Patent: Feb. 26, 2019

(54) ORAL COMPOSITIONS AND USES THEROF

(75) Inventors: Andrew Nowak, Los Angeles, CA (US); James Masters, Ringoes, NJ (US); Shira Pilch, Highland Park, NJ (US)

(73) Assignee: Colgate-Palmolive Company, New York, NY (US)

( * ) Notice: Subject to any disclaimer, the term of this patent is extended or adjusted under 35 U.S.C. 154(b) by 421 days.

(21) Appl. No.: 12/992,989

(22) PCT Filed: May 15, 2009

(86) PCT No.: PCT/US2009/044100
§ 371 (c)(1),
(2), (4) Date: Feb. 8, 2011

(87) PCT Pub. No.: WO2009/140577
PCT Pub. Date: Nov. 19, 2009

(65) Prior Publication Data
US 2012/0100193 A1    Apr. 26, 2012

Related U.S. Application Data

(60) Provisional application No. 61/053,863, filed on May 16, 2008.

(51) Int. Cl.
*A61Q 11/00* (2006.01)
*A61K 8/02* (2006.01)
*A61K 8/25* (2006.01)

(52) U.S. Cl.
CPC ............ *A61Q 11/00* (2013.01); *A61K 8/0241* (2013.01); *A61K 8/25* (2013.01); *A61K 2800/28* (2013.01); *A61K 2800/412* (2013.01); *A61K 2800/651* (2013.01)

(58) Field of Classification Search
CPC ........ A61Q 11/00; A61K 8/0241; A61K 8/25; A61K 2800/651; A61K 2800/412; A61K 2800/28
See application file for complete search history.

(56) References Cited

U.S. PATENT DOCUMENTS

| | | | |
|---|---|---|---|
| 3,535,421 A | 10/1970 | Briner et al. |
| 3,696,191 A | 10/1972 | Weeks |
| 3,937,807 A | 2/1976 | Haefele |
| 3,959,458 A | 5/1976 | Agricola et al. |
| 3,991,177 A | 11/1976 | Vidra et al. |
| 4,051,234 A | 9/1977 | Gieske |
| 4,058,595 A | 11/1977 | Colodney |
| 4,154,815 A | 5/1979 | Pader |
| 4,340,583 A | 7/1982 | Wason |
| 4,355,022 A | 10/1982 | Rabussay |
| 4,420,312 A | 12/1983 | Wason |
| 4,421,527 A | 12/1983 | Wason |
| 4,842,847 A | 6/1989 | Amjad |
| 4,894,220 A | 1/1990 | Nabi et al. |
| 4,992,420 A | 2/1991 | Neeser |
| 5,000,939 A | 3/1991 | Dring et al. |
| 5,004,597 A | 4/1991 | Majeti et al. |
| 5,292,526 A | 3/1994 | Gaffar et al. |
| 5,651,958 A | 7/1997 | Rice |
| 5,658,533 A | 8/1997 | Holm |
| 5,939,051 A | 8/1999 | Santalucia et al. |
| 6,290,933 B1 | 9/2001 | Durga et al. |
| 6,379,654 B1 | 4/2002 | Gebreselassie et al. |
| 6,416,744 B1 | 7/2002 | Robinson et al. |
| 6,555,094 B1 | 4/2003 | Glandorf et al. |
| 6,616,916 B1 | 9/2003 | Karpe et al. |
| 6,651,958 B1 | 11/2003 | James et al. |
| 6,669,929 B1 | 12/2003 | Boyd et al. |
| 6,706,256 B2 | 3/2004 | Lawlor |
| 2003/0131536 A1 | 7/2003 | Kostinko et al. |
| 2003/0206874 A1 | 11/2003 | Doyle et al. |
| 2006/0008423 A1 | 1/2006 | Araya et al. |
| 2006/0110339 A1 | 5/2006 | McGill et al. |
| 2006/0140878 A1 | 6/2006 | Cornelius et al. |
| 2007/0014741 A1 | 1/2007 | Chiu |
| 2008/0181856 A1 | 7/2008 | Prencipe |

FOREIGN PATENT DOCUMENTS

| | | |
|---|---|---|
| JP | 2009-531428 A | 9/2009 |
| WO | WO 1995/033441 | 12/1995 |
| WO | WO 1996/009809 | 4/1996 |
| WO | WO 1996/034592 | 11/1996 |
| WO | WO01/85115 | 5/2002 |
| WO | WO 2004/032647 | 4/2004 |
| WO | WO 2004/032674 | 4/2004 |
| WO | WO2004/043419 | 5/2004 |
| WO | WO2004/045504 | 6/2004 |

(Continued)

OTHER PUBLICATIONS

GR Stookey et al. "In Vitro Removal of Stain with Dentifrice," J. Dent. Res. 61 (11) (1982): 1236-1239.

(Continued)

*Primary Examiner* — Trevor Love

(57) ABSTRACT

The present invention is directed to oral compositions comprising an orally-acceptable carrier and a silica abrasive comprising a precipitated amorphous silica compound having an average particle size of from 5 μm to 20 μm, oil absorption of from 60 cc/100 g to 120 cc/100 g, and an Einlehner hardness of from 4 to 11, and methods of use thereof.

13 Claims, No Drawings

(56) References Cited

FOREIGN PATENT DOCUMENTS

| WO | WO 2005/065634 |   | 7/2005  |              |
|----|----------------|---|---------|--------------|
| WO | WO 2005/067877 |   | 7/2005  |              |
| WO | WO 2006/022848 | * | 3/2006  | ...... A61K 7/16 |
| WO | WO 2006/038318 |   | 4/2006  |              |
| WO | WO2006/057716  |   | 6/2006  |              |
| WO | WO2006/057717  |   | 6/2006  |              |
| WO | WO2006/057718  |   | 6/2006  |              |
| WO | WO 2007/068916 |   | 6/2007  |              |
| WO | WO2007/078630  |   | 7/2007  |              |
| WO | WO2007/078651  | * | 7/2007  | ...... A61K 8/97 |
| WO | WO2007/094891  |   | 8/2007  |              |
| WO | WO2007/111877  |   | 10/2007 |              |
| WO | WO2007/134003  |   | 11/2007 |              |

OTHER PUBLICATIONS

Hefferren, J. Dent Res 55 (1976) p. 563-573. Determination of the abrasion on the dentin (dentin).

PCT Search report for PCT/US09/044100 filed May 15, 2009 dated Oct. 8, 2009.

Huber Dental Silicas, 2010, "Zeodent® High Performing Dental Silicas: Engineered to Deliver Exceptional Performance and Fornmlating Flexibility," http://www.hubermaterials.com/userfiles/files/PDFDocs/Zeodent High Performing Dental Silicas (European Version).pdf [retrieved Jan. 15, 2014].

\* cited by examiner

ORAL COMPOSITIONS AND USES THEROF

CROSS-REFERENCE TO RELATED PATENT APPLICATIONS

The present application is a national stage entry under 35 U.S.C. § 371 of International Patent Application No. PCT/US2009/044100, filed May 15, 2009, which claims priority to U.S. Provisional Application No. 61/053,863, filed May 16, 2008, the entireties of which are hereby incorporated by reference.

BACKGROUND OF THE INVENTION

Abrasives in oral compositions debride and physically scrub the external surface of the teeth. This scrubbing action removes organic biofilm (i.e., the pellicle) on the tooth surface that is formed primarily of salivary proteins, bacteria, and bacterial byproducts. Pellicle may also be stained and discolored by foods, such as coffee, tea and berries, as well as, by tobacco smoke, cationic compounds, and chromogenic bacteria. Such physical removal of the stained pellicle is a simple and effective means of removing the undesirable surface staining and discoloration which occurs daily. Further, such physical removal of the pellicle also removes plaque bacteria on the pellicle surface, thereby minimizing the potential for gingivitis, periodontitis, and caries formation. However, oral compositions such as dentifrices should not have such high abrasiveness that potential damage to the enamel or tissue may result. As such, it is desirable to develop oral compositions that optimize the cleaning and/or polishing efficacy of the oral composition, while minimizing the harmful abrasiveness to avoid potential damage oral surfaces. Preferably, such oral compositions have a high pellicle cleaning ratio (PCR), but a low degree of dental abrasion, which is measured as radioactive dental abrasion (RDA).

In commonly accepted conventional practice, RDA values for an oral composition are generally kept below 250 to avoid harming enamel/dentin with repeated usage. However, in order to achieve a higher PCR, typically the amount and hardness of abrasives must be increased, which is conventionally known to increase the RDA. For example, it has been observed that when the RDA value of a dentifrice composition exceeds certain values, such as, e.g., above 100 to 115, the dentifrice does not necessarily exhibit a corresponding increase in the cleaning performance of the dentifrice. It has been challenging to formulate oral compositions that have a PCR of greater than 80 or 90 but still have an RDA that is below 250.

BRIEF SUMMARY OF THE INVENTION

It has been surprisingly discovered that the use of particular silica abrasives in oral care compositions imparts a superior cleaning ability, e.g., a high PCR value, and at the same time, reduces damage to hard dental surfaces, e.g., a low PDA. The silica abrasives useful in the present invention maintain their integrity while abrading soft matter on tooth surfaces, such as plaque and pellicle. However, the silica abrasive breaks down or fracture under shear forces, e.g., during brushing, as a result of interacting with hard enamel or dentin surfaces. In this regard, the oral compositions of the present invention provide a superior cleaning and/or polishing efficacy, while achieving a desirably low RDA that minimizes potential damage to enamel or dentin. Additionally, the compositions of the present invention may provide cleaning and/or polishing of a tooth surface. Cleaning and/or polishing abrasives can be classified by various physical parameters. As appreciated by one of skill in the art, a single abrasive species typically performs at least some cleaning and polishing simultaneously.

In one embodiment, the present invention is directed to Composition 1.0, an oral composition comprising an orally-acceptable carrier and a silica abrasive comprising a silica compound having an average particle size of from 5 µm to 20 µm, and an Einlehner hardness of from 4 to 11.

Additional compositions of the present invention the following compositions:

1.1 Composition 1.0 wherein the silica abrasive has an average particle size of from 8 µm to 11 µm, e.g., from 9 µm to 13 µm.

1.2 Composition 1.0 or 1.1 wherein the silica abrasive has an oil absorption of from 60 cc/100 g to 120 cc/100 g, e.g., from 70 cc/100 g to 110 cc/100 g, e.g., from 80 cc/100 g to 100 cc/100 g, e.g., linseed oil absorption.

1.3 Any one of the preceding compositions wherein the silica abrasive has an Einlehner hardness of from 5 to 10, e.g., from 6 to 9.

1.4 Any one of the preceding compositions having a pellicle cleaning ratio (PCR) of from 80 to 105, e.g., from 85 to 100, or from 90 to 95;

1.5 Any one of the preceding compositions having a radioactive dentin abrasion (RDA) of less than 150, e.g., from 90 to 130, from 100 to 120, or from 105 to 115;

1.6 Any one of the preceding compositions having a PCR/RDA ratio of from 0.5 to 1.5, e.g., 0.8, or 1;

1.7 Any one of the preceding compositions wherein the silica abrasive is from 1% to 95% by weight of the composition.

1.8 Any one of the preceding compositions wherein the silica abrasive has a $d_{10}$ of from 2.5 µm to 2.9 µm;

1.9 Any one of the preceding compositions wherein the silica abrasive fragments when the oral composition is applied to a hard surface, e.g., enamel or dentin, in the oral cavity;

1.10 Any one of the preceding compositions wherein upon use of the composition in the oral cavity, the silica abrasive fragments into particles having a $d_{10}$ of from 2.3 µm to 2.6 µm;

1.11 Any one of the preceding compositions wherein the silica abrasive fragments when subjected to shear forces for sufficient amount of time.

1.12 Any one of Composition 1.9-1.11 wherein the oral composition is brushed on the teeth, e.g., for at least 30 seconds to 5 minutes;

1.13 Any one of compositions Composition 1.9-1.12 wherein the mean particle size of the silica abrasive is reduced from 16% to 20% after being applied to a hard surface in the oral cavity;

1.14 Any one of compositions 1.9-1.13 wherein the $d_{10}$ of the silica abrasive is reduced from 9% to 12% after being applied to a hard surface in the oral cavity.

1.15 Any one of the preceding compositions comprising an effective amount of a fluoride salt, e.g., from 0.01 wt. % to 2 wt. %, e.g., 0.1 to 0.2 wt. % of the total composition weight.

1.16 Any one of the preceding compositions comprising a fluoride ion source comprising a fluoride salt selected from stannous fluoride, sodium fluoride, potassium fluoride, sodium monofluorophosphate, sodium fluorosilicate, ammonium fluorosilicate, amine fluoride, amine fluoride ammonium fluoride, and combinations thereof;

1.17 Any of the preceding compositions comprising from 500 to 5000, from 1000 to 1500, or 1450 ppm fluoride ion.

1.18 Any of the preceding compositions comprising at least one surfactant.

1.19 Any of the preceding compositions comprising at least one surfactant selected from sodium lauryl sulfate, cocamidopropyl betaine, and combinations thereof.

1.20 Any of the preceding compositions comprising an anionic surfactant.

1.21 Any of the preceding compositions comprising sodium lauryl sulfate.

1.22 Any of the preceding compositions comprising at least one humectant.

1.23 Any of the preceding compositions comprising at least one humectant selected from glycerin, sorbitol and combinations thereof.

1.24 Any of the preceding compositions comprising at least one polymer.

1.25 Any of the preceding compositions comprising at least one polymer selected from polyethylene glycols, polyvinylmethyl ether maleic acid copolymers, polysaccharides (e.g. cellulose derivatives, for example carboxymethyl cellulose, or polysaccharide gums, for example xanthan gum or carrageenan gum), and combinations thereof 1.26 Any of the preceding compositions comprising flavoring, fragrance and/or coloring.

1.27 Any of the preceding compositions comprising an antibacterial agent.

1.28 Any of the preceding compositions comprising an antibacterial agent selected from a halogenated diphenyl ether (triclosan), herbal extracts or essential oils (e.g. rosemary extract, thymol, menthol, eucalyptol, methyl salicylate), bisguanide antiseptics (e.g., chlorhexidine, alexidine or octenidine), quaternary ammonium compounds (e.g., cetylpyridinium chloride), phenolic antiseptics, hexetidine, povidone iodine, delmopinol, salifluor, metal ions (e.g., zinc salts, for example, zinc citrate), sanguinarine, propolis and oxygenating agents (e.g., hydrogen peroxide, buffered sodium peroxyborate or peroxycarbonate).

1.29 Any of the preceding compositions comprising triclosan.

1.30 Any of the preceding compositions comprising an antibacterial agent in an amount of 0.01-5, 0.01-1.0, or 0.3 wt. % of the total composition weight.

1.31 Any of the preceding compositions comprising a tooth desensitizing agent;

1.32 Any of the preceding compositions comprising a tooth desensitizing agent selected from a potassium salt, capsaicin, eugenol, a strontium salt, a zinc salt, a chloride salt, or combinations thereof.

1.33 Any of the preceding compositions comprising a tooth whitening compound;

1.34 Any of the preceding compositions which is a tooth powder;

1.35 Any of the preceding compositions comprising water, 1.36 Any of the preceding compositions which is a toothpaste or gel.

1.37 Any one of the preceding compositions wherein the RDA of the oral composition is calculated by a method comprising applying 1-5 ml of a slurry of the oral composition to a 1-10 cm$^2$ surface; contacting the surface against a $^{32}$P irridated tooth; brushing the tooth with the surface for 300 strokes at a constant force of 2 to 5 newtons, wherein each stroke causes the surface to move from 1-10 cm$^2$ against the tooth, and measuring the RDA value.

1.38 Any of the preceding compositions wherein the RDA of the composition decreases over time as the composition is utilized in the oral cavity, e.g., contacted with a hard dental surface, and the RDA of the oral composition is calculated by the method identified in 1.37, with the provisio that the number of strokes utilized at an initial time A is less than the number of strokes used at a later time B, e.g., 300 strokes equals approximately two minutes of brushing;

1.39 Any one of the preceding compositions wherein the RDA of the oral composition used in the oral cavity for five seconds is from 1.3 to 1.6 times the RDA of the composition when used in the oral cavity for 1-5 minutes, e.g., 2, 3, or 4 minutes.

1.40 Composition 1.39 wherein the surface is the cleaning head of a toothbrush;

1.41 Composition 1.39 or 1.40 wherein the method of calculating the RDA wherein the slurry comprises from 50% to 100% by weight of the oral composition.

1.42 Any of the preceding compositions wherein Einlehner hardness is measured per 174,000 revolutions with a Brass screen.

1.43 Any one of compositions 1.0-1.41 wherein Einlehner hardness is measured per 100,000 revolutions with a brass screen.

1.44 Composition 1.42 or 1.43 wherein Einlehner hardness is of a slurry of 100 g silica abrasive in 1 L water.

1.45 Any of the preceding compositions wherein a 10% aqueous slurry of the silica abrasive has a PCR of from 65 to 80, e.g., from 68 to 76, or 72.

1.46 Any of the preceding compositions wherein a 10% aqueous slurry of the silica abrasive has a RDA of from 75 to 91, e.g., from 79 to 87, or 83;

1.47 Any of the preceding compositions wherein a 10% aqueous slurry of the silica abrasive has a PCR/RDA ratio of from 0.7 to 0.9, e.g., from 0.8 to 0.9, e.g., 0.86;

1.48 Any of the preceding compositions wherein a 15% aqueous slurry of the silica abrasive has a PCR of from 68 to 84, e.g., from 62 to 80, or 76.

1.49 Any of the preceding compositions wherein a 15% aqueous slurry of the silica abrasive has a RDA of from 85 to 105, e.g., from 90 to 100, or 95;

1.50 Any of the preceding compositions wherein a 15% aqueous slurry of the silica abrasive has a PCR/RDA ratio of from 0.7 to 0.9, e.g., from 0.76 to 0.8, e.g., 0.86;

1.51 Any of the preceding compositions wherein a 20% aqueous slurry of the silica abrasive has a PCR of from 76 to 92, e.g., from 80 to 88, or 84.

1.52 Any of the preceding compositions wherein a 20% aqueous slurry of the silica abrasive has a RDA of from 85 to 101, e.g., from 89 to 97, or 93;

1.53 Any of the preceding compositions wherein a 20% aqueous slurry of the silica abrasive has a PCR/RDA ratio of from 0.8 to 1.0, e.g., from 0.85 to 0.95, e.g., 0.9;

1.54 Any of the preceding compositions wherein a 30% aqueous slurry of the silica abrasive has a PCR of from 78 to 94, e.g., from 82 to 90, or 86.

1.55 Any of the preceding compositions wherein a 30% aqueous slurry of the silica abrasive has a RDA of from 100 to 124, e.g., from 106 to 118, or 112;

1.56 Any of the preceding compositions wherein a 30% aqueous slurry of the silica abrasive has a PCR/RDA ratio of from 0.6 to 0.9, e.g., from 0.7 to 0.8, e.g., 0.77.

1.57 Composition 1.0, wherein the silica abrasive has a median particle size of from 8 μm to 11 μm, such as, but not limited to, from 9 μm to 13 μm, from 8 μm to 12 μm, or from 8 μm to 11 μm.

1.58 Any one of compositions Composition 1.9-1.12 wherein the median particle size of the silica abrasive is reduced from 16% to 20% after being applied to a hard surface in the oral cavity;

The silica compound which is used as an abrasive in the present invention may be an amorphous silica, a precipitated silica, or an amorphous precipitated silica. In one embodiment, the silica abrasive consists essentially of the silica compound as described herein. The silica abrasive as described herein may function as a tooth cleaning agent, tooth polishing agent, and/or an antisensitivity agent.

An additional aspect of the present invention involves the surprising discovery that the fractured silica abrasive particles may aid in the treatment of tooth sensitivity, in that the fractured particles may plug tubule occlusions. Additionally, it has also been surprising found that the smaller particles are more effective in removing debris and stain from crevices in the oral cavity, particularly the interproximal surfaces of teeth.

The present invention also encompasses Method 2.0, a method to improve oral health comprising applying an effective amount of the oral composition of any of the embodiments under Compositions 1.0-1.55 to the oral cavity of a subject in need thereof, e.g. a method to
1. reduce or inhibit formation of dental caries,
2. reduce, repair or inhibit pre-carious lesions of the enamel, e.g., as detected by quantitative light-induced fluorescence (QLF) or electrical conductance measurement (ECM),
3. reduce or inhibit demineralization and promote remineralization of the teeth,
4. reduce hypersensitivity of the teeth,
5. reduce or inhibit gingivitis,
6. inhibit microbial biofilm formation in the oral cavity,
7. reduce plaque accumulation, and/or
8. clean the teeth and oral cavity.

Other embodiments of the present invention will be apparent to one of skill in the art.

DETAILED DESCRIPTION OF THE INVENTION

As used herein, all measurement levels described herein are by weight of the total composition, unless otherwise indicated. Additionally, all references cited herein are hereby incorporated by reference in their entireties. However, in the event of a conflict between any definitions in the present disclosure and those in a cited reference, the present disclosure controls.

"Safe and effective amount" as used herein means a sufficient amount to treat the oral cavity, e.g., reduce plaque, gingivitis, and/or stain without harming the tissues and structures of the oral cavity.

An "orally acceptable carrier" as used herein means a material or materials which are used to apply the compositions of the present invention to the oral cavity in a safe and effective manner.

As used herein, "cleaning" generally refers to the removal of contaminants, dirt, impurities, and/or extraneous matter on a target surface. For example, in the context of oral surfaces, where the surface is tooth enamel, the cleaning may remove at least some of a film or stain, such as plaque biofilm, pellicle or tartar.

As used herein, "polishing" generally refers to a finishing or refining process that makes a surface smoother and/or glossier. Polishing and cleaning can also provide brightening of the surface where stain removal occurs, for example, whitening of a tooth surface.

In various embodiments, an oral composition is provided that has an abrasive. Preferably, the silica abrasive is a precipitated amorphous silica compound.

The silica of the present invention may have a mean particle size of from 5 μm to 205 μm. Mean particle size of particles may be measured by any means known in the art. For example, mean particle size may be measured using a Malvern Particle Size Analyzer, Model Mastersizer S, Malvern Instruments, Inc. (Southborough, Mass., USA), wherein a helium-neon gas laser beam is projected through a transparent cell that contains the abrasive suspended in an aqueous solution. Light rays that strike the particles are scattered through angles that are inversely proportional to the particle size. The photodetector array measures the quantity of light at several predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the subject abrasive. The mean particle size takes into account skewed particle sizes and the size distribution of the particles.

As used herein, $d_{10}$ refers to particles having a diameter that is 10% of the threshold of the sampled population (i.e., 10% of the population is equal to or smaller than the $d_{10}$ value).

It has been surprisingly found that the abrasive particles, when incorporated into an oral composition, break down or fracture as the oral composition is brushed against hard dental surfaces, e.g., dentin or enamel. It has also been surprisingly found that the abrasive particles, when incorporated into an oral composition, substantially retain their original size when as the oral composition is brushed against soft surfaces of the oral cavity, or soft biofilms, e.g., pellicle or plaque.

The silica abrasive of the present invention may have a specific oil absorption of from 60 cc/100 g to 120 cc/100 g linseed oil. In an embodiment, the silica abrasive has an oil absorption of from 70 cc/100 g to 110 cc/100 g. In an embodiment, the silica abrasive has an oil absorption of from, from 80 cc/100 g to 100 cc/100 g. In an embodiment, the silica abrasive has an oil absorption of 40 cc/100 g to 60 cc/100 g. Oil absorption may be determined by various means known by those of skill in the art. For example, oil absorption may be determined by absorption of linseed oil or dibutyl phthalate (DBP) per 100 grams or abrasive. Oil absorption values can be measured using the ASTM Rub-Out Method D281.

The abrasives of the present invention may have a specific Einlehner hardness of from 4 to 11. Einlehner hardness may be determined by various means known by those of skill in the art. For example, an Einlehner At-1000 Abrader may measure the hardness of the abrasive particle in the following manner: a Fourdrinier metal screen, i.e., copper or brass, is weighed and exposed to the action of a suspension of the abrasive (for example, a 10% aqueous suspension of the abrasive) for a given number of revolutions. The hardness value is expressed as milligrams weight lost of the Fourdrinier wire screen per number of revolutions, e.g., 100,000 revolutions. In the present invention, Einlehner hardness of the silica abrasive utilized in the present invention is determined by utilizing a brass screen. 100 g of silica is added to 1 L of water, and the slurry is rotated for 100,000 or 174,000 revolutions.

The abrasive component of the present invention may be incorporated into an oral care product fat a level of from 1% to 95% by weight. The amount off abrasive present depends on the particular format of the oral care composition. For example, when the oral care composition is a toothpaste or gel, it may contain from 1% to 75% of the abrasive. When the oral care composition is a toothpowder, it may contain from 50% to 95% of the abrasive.

PCR is a known method by those of skill in the art to measure the efficacy of removing tooth stains relative to a standard. The PCR values referred to herein are obtained by a modification of the method described in "In Vitro Removal of Stain with Dentifrice", G. K. Stookey, et al J. Dental Research, 61, 123-9 (1982). The modification of the PCR method used herein is described in U.S. Pat. Nos. 5,658,553 and 5,651,958 both to Rice. In this modification, a clear pellicle material is applied to a bovine tooth first, which is then stained with a combination of the pellicle material and tea, coffee and $FeCl_3$ whereas in the original method described by Stookey et al. both pellicle and stain are applied simultaneously. The compositions of the present invention may have a PCR of from 80 to 105. In an embodiment, the PCR is from 85 to 100. In another aspect, the PCR is from 90 to 95.

The compositions of the present invention may have a RDA value of less than 150, e.g., from 90 to 130, from 100 to 120, or from 105 to 115. RDA values may be determined by any number of methods known by those of skill in the art. For example, RDA values may be determined according to the method set forth in U.S. Pat. Nos. 4,340,583, 4,420,312, and 4,421,527, and Hefferren, Journal of Dental Research, July-August 1976, pages 563-573. Generally, irradiated $^{32}P$ dentin is brushed, e.g., with an oral composition. The amount of dentin that is abraded away from the brushed dentin is quantified via analysis of $^{32}P$ which is observed in the abrasive slurry. The amount of dentin abrasion is referenced to a standard composition brushed on to the dentin, usually calcium pyrophosphate, which is set at an RDA value of 100. Generally, less abrasive compositions have lower RDA values.

The compositions of the present invention may have a PCR/RDA ratio of from 0.5 to 1.5. In an embodiment, the PCR/RDA ratio may be 0.5, 0.6, 0.7, 0.8, 0.9, 1.0, 1.1, 1.2, 1.3, 1.4 or 1.5. The PCR/RDA ratio is used to determine the relative ration of cleaning and abrasion characteristics of an oral care composition, e.g., a dentifrice or toothpaste composition.

Useful silica abrasive materials for preparing the oral compositions of the present invention may be obtained from Davison Chemical Division of W. R. Grace & Co. (Baltimore, Md., USA) under the tradename GRACE VP5. In an embodiment, the silica is an INEOS (now PQ Corp.) Sorbosil AC43 silica. In an embodiment, AC43 silica has properties including, but not limited to, an average particle size of 2.7-4.0 microns (as determined by MALVERN MASTERSIZER), a sieve residue of +45 µm, moisture loss at 105° C. of 8.0% max, an ignition loss at 1000° C. of 14.0% max, and a pH of 5.5-7.5 in aqueous suspension.

Other abrasives may also be utilized in the present compositions, though it is contemplated that the compositions of the present invention may contain a single silica abrasive compound as previously described, and may be substantially free of other silicon or silica abrasives and compounds.

Orally acceptable carriers are well known in the art, and may include surfactants, humectants, thickeners, foaming agents, fluoride ion source, flavorings, colors, chelating agents, polymers, enzymes, water, actives, and other materials. The oral compositions may further comprise an orally acceptable carrier. The specific composition of the carrier depends on the intended use of the composition. The carrier can be a liquid, semi-solid, or solid phase. Oral compositions can be in the form of a dentifrice (including toothpastes, toothpowders, and prophylaxis pastes), confectionaries (including gums, beads and chews), film, paint-on gels, or any other form known to one of skill in the art where abrasives are employed. Selection of specific carrier components is dependent on the desired product form.

The active ingredients include for example, anti-bacterial active agents, anti-tartar agents, anti-caries agents, anti-inflammatory agents, anti-sensitivity agents, enzymes, nutrients, and the like. Actives useful herein are optionally present in the compositions of the present invention in safe and effective amounts that are sufficient to have the desired therapeutic or prophylactic effect in the human or lower animal subject to whom the active is administered, without undue adverse side effects (such as toxicity, irritation, or allergic response), commensurate with a reasonable risk/benefit ratio when used in the manner of this invention. The specific safe and effective amount of the active will vary with such factors as the particular condition being treated, the physical condition of the subject, the nature of concurrent therapy (if any), the specific active used, the specific dosage form, the carrier employed, and the desired dosage regimen. Active ingredients useful for treating such conditions include those discussed in United States Patent Publication 2003/0206874 to Doyle et al. Actives among those useful herein are also discussed in U.S. Pat. No. 6,290,933 to Durga et al. and U.S. Pat. No. 6,685,921 to Lawlor.

Fluoride salts and fluoride ion sources, e.g., fluoride salts which may be soluble, are well known in the art and may be incorporated into the compositions of the present invention. Representative fluoride ion sources include, but are not limited to, stannous fluoride, sodium fluoride, potassium fluoride, sodium monofluorophosphate, sodium fluorosilicate, ammonium fluorosilicate, amine fluoride, ammonium fluoride, and combinations thereof. In certain embodiments the fluoride ion source includes stannous fluoride, sodium fluoride, amine fluorides, sodium monofluorophosphate, as well as mixtures thereof. In certain embodiments, the oral care composition of the invention may also contain a source of fluoride ions or fluorine-providing ingredient in amounts sufficient to supply 25 ppm to 5,000 ppm of fluoride ions, generally at least 500 ppm, e.g., 500 to 2000 ppm, e.g., 1000-1600 ppm, e.g., 1450 ppm. Fluoride ion sources may be added to the compositions of the invention at a level of 0.01 wt. % to 10 wt. % in one embodiment or 0.03 wt. % to 5 wt. %, and in another embodiment 0.1 wt. % to 1 wt. % by weight of the composition in another embodiment; however, it is to be understood that the weights of fluoride salts to provide the appropriate level of fluoride ion will obviously vary based on the weight of the counter ion in the salt, and one of skill in the art may readily determine such amounts.

The oral care compositions of the invention may include one or more agents to increase the amount of foam that is produced when the oral cavity is brushed. Such foaming agents are known to those of skill in the art. Illustrative examples of agents that increase the amount of foam include, but are not limited to polyoxyethylene and certain polymers including, but not limited to, alginate polymers. The polyoxyethylene may increase the amount of foam and the thickness of the foam generated by the oral care carrier component of the present invention. Polyoxyethylene is also commonly known as polyethylene glycol ("PEG") or polyethylene oxide. The polyoxyethylenes suitable for this invention will have a molecular weight of 200,000 to 7,000,000. In one embodiment the molecular weight will be 600,000 to 2,000,000 and in another embodiment 800,000 to 1,000,000. The polyoxyethylene may be present in an amount of 1% to 90%, in one embodiment 5% to 50% and in another embodiment 10% to 20% by weight of the oral care carrier component of the oral care compositions of the present invention. The dosage of foaming agent in the oral care composition (i.e., a single dose) is 0.01 to 0.9% by weight, 0.05 to 0.5% by weight, and in another embodiment 0.1 to 0.2% by weight.

The compositions of the present invention may also incorporate one or more surfactants which are known in the art. Suitable surfactants include those which are reasonably stable throughout a wide pH range, for example, anionic, cationic, nonionic or zwitterionic surfactants. Suitable surfactants are described more fully, for example, in U.S. Pat. No. 3,959,458, to Agricola et al.; U.S. Pat. No. 3,937,807, to Haefele; and U.S. Pat. No. 4,051,234, to Gieske et al., which are incorporated herein by reference. In certain embodiments, the anionic surfactants useful herein include the water-soluble salts of alkyl sulfates having 10 to 18 carbon atoms in the alkyl radical and the water-soluble salts of sulfonated monoglycerides of fatty acids having 10 to 18 carbon atoms. Sodium lauryl sulfate, sodium lauroyl sarcosinate and sodium coconut monoglyceride sulfonates are examples of anionic surfactants of this type. Mixtures of anionic surfactants may also be utilized. In another embodiment, cationic surfactants useful in the present invention can be broadly defined as derivatives of aliphatic quaternary ammonium compounds having one long alkyl chain containing 8 to 18 carbon atoms such as lauryl trimethylammonium chloride, cetyl pyridinium chloride, cetyl trimethylammonium bromide, di-isobutylphenoxyethyldimethylbenzylammonium chloride, coconut alkyltrimethylammonium nitrite, cetyl pyridinium fluoride, and mixtures thereof. Illustrative cationic surfactants are the quaternary ammonium fluorides described in U.S. Pat. No. 3,535,421, to Briner et al., herein incorporated by reference. Certain cationic surfactants can also act as germicides in the compositions. In one embodiment of the present invention, the oral compositions are substantially free of cationic surfactants. Illustrative nonionic surfactants that can be used in the compositions of the invention can be broadly defined as compounds produced by the condensation of alkylene oxide groups (hydrophilic in nature) with an organic hydrophobic compound which may be aliphatic or alkylaromatic in nature. Examples of suitable nonionic surfactants include, but are not limited to, the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials. In certain embodiments, zwitterionic synthetic surfactants useful in the present invention can be broadly described as derivatives of aliphatic quaternary ammonium, phosphomium, and sulfonium compounds, in which the aliphatic radicals can be straight chain or branched, and wherein one of the aliphatic substituents contains 8 to 18 carbon atoms and one contains an anionic water-solubilizing group, e.g., carboxy, sulfonate, sulfate, phosphate or phosphonate. Illustrative examples of the surfactants suited for inclusion into the composition include, but are not limited to, sodium alkyl sulfate, sodium lauroyl sarcosinate, cocoamidopropyl betaine and polysorbate 20, and combinations thereof.

The compositions of the present invention may comprise an anionic surfactant, e.g., sodium lauryl sulfate. The surfactant or mixtures of compatible surfactants can be present in the compositions of the present invention in 0.1% to 5.0%, in another embodiment 0.3% to 3.0% and in another embodiment 0.5% to 2.0% by weight of the total composition.

The compositions of the invention may also include one or more flavoring agents known by those of skill in the art. Flavoring agents which are used in the practice of the present invention include, but are not limited to, essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Certain embodiments employ the oils of peppermint and spearmint. The flavoring agent is incorporated in the oral composition at a concentration of 0.1 to 5% by weight and 0.5 to 1.5% by weight. The dosage of flavoring agent in the individual oral care composition dosage (i.e., a single dose) is 0.001 to 0.05% by weight and in another embodiment 0.005 to 0.015% by weight.

The oral care compositions of the invention also may optionally include one or more chelating agents able to complex calcium found in the cell walls of the bacteria. Binding of this calcium weakens the bacterial cell wall and augments bacterial lysis. Another group of chelating agents which may be useful in the present invention are soluble pyrophosphates. Pyrophosphate salts used in the present compositions can be any of the alkali metal pyrophosphate salts. In certain embodiments, salts include tetra alkali metal pyrophosphate, dialkali metal diacid pyrophosphate, trialkali metal monoacid pyrophosphate and mixtures thereof, wherein the alkali metals are sodium or potassium. The salts are useful in both their hydrated and unhydrated forms. An effective amount of pyrophosphate salt useful in the present composition is generally enough to provide at least 1.0 wt. % pyrophosphate ions, 1.5 wt. % to 6 wt. %, 3.5 wt. % to 6 wt. % of such ions.

The oral care compositions of the invention also optionally include one or more polymers, such as polyethylene glycols, polyvinylmethyl ether maleic acid copolymers, polysaccharides (e.g. cellulose derivatives, for example carboxymethyl cellulose, or polysaccharide gums, for example xanthan gum or carrageenan gum). Acidic polymers, for example polyacrylate gels, may be provided in the form of their free acids or partially or fully neutralized water soluble alkali metal (e.g. potassium and sodium) or ammonium salts. Certain embodiments include 1:4 to 4:1 copolymers of maleic anhydride or acid with another polymerizable ethylenically unsaturated monomer, for example, methyl vinyl ether (methoxyethylene) having a molecular weight (M.W.) of 30,000 to 1,000,000. These copolymers are available for example as Gantrez AN 139 (M.W. 500,000), AN 119 (M.W. 250,000) and S-97 Pharmaceutical Grade (M.W. 70,000), of GAF Chemicals Corporation. Other operative polymers include those such as the 1:1 copolymers of maleic anhydride with ethyl acrylate, hydroxyethyl methacrylate, N-vinyl-2-pyrollidone, or ethylene, the latter being available for example as Monsanto EMA No. 1103, M.W. 10,000 and EMA Grade 61, and 1:1 copolymers of acrylic acid with methyl or hydroxyethyl methacrylate, methyl or ethyl acrylate, isobutyl vinyl ether or N-vinyl-2-pyrrolidone. Suitable generally, are polymerized olefinically or ethylenically unsaturated carboxylic acids containing an activated carbon-to-carbon olefinic double bond and at least one carboxyl group, that is, an acid containing an olefinic double bond which readily functions in polymerization because of its presence in the monomer molecule either in the alpha-beta position with respect to a carboxyl group or as part of a terminal methylene grouping. Illustrative of such acids are acrylic, methacrylic, ethacrylic, alpha-chloroacrylic, crotonic, beta-acryloxy propionic, sorbic, alpha-chlorsorbic, cinnamic, beta-styrylacrylic, muconic, itaconic, citraconic, mesaconic, glutaconic, aconitic, alpha-phenylacrylic, 2-benzyl acrylic, 2-cyclohexylacrylic, angelic, umbellic, fumaric, maleic acids and anhydrides. Other different olefinic monomers copolymerizable with such carboxylic monomers include vinylacetate, vinyl chloride, dimethyl maleate and the like. Copolymers contain sufficient carboxylic salt groups for water-solubility. A further class of polymeric agents includes a composition containing homopolymers of substituted acrylamides and/or homopolymers of unsaturated sulfonic acids and salts thereof, in particular where polymers are based on unsaturated sulfonic acids selected from acrylamidoalykane sulfonic acids such as 2-acrylamide 2 methylpropane sulfonic acid having a molecular weight of 1,000 to 2,000,000, described in U.S. Pat. No. 4,842,847, Jun. 27, 1989 to Zahid, incorporated herein by reference.

In preparing oral care compositions, it is sometimes necessary to add some thickening material to provide a desirable consistency or to stabilize or enhance the performance of the formulation. In certain embodiments, the thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as karaya, gum arabic, and gum tragacanth can also be incorporated. Colloidal magnesium aluminum silicate or finely divided silica can be used as component of the thickening composition to further improve the composition's texture. In certain embodiments, thickening agents in an amount of 0.5% to 5.0% by weight of the total composition are used.

The oral care compositions of the invention may also optionally include one or more enzymes. Useful enzymes include any of the available proteases, glucanohydrolases, endoglycosidases, amylases, mutanases, lipases and mucinases or compatible mixtures thereof. In certain embodiments, the enzyme is a protease, dextranase, endoglycosidase and mutanase. In another embodiment, the enzyme is papain, endoglycosidase or a mixture of dextranase and mutanase. Additional enzymes suitable for use in the present invention are disclosed in U.S. Pat. No. 5,000,939 to Dring et al., U.S. Pat. Nos. 4,992,420; 4,355,022; 4,154,815; 4,058,595; 3,991,177; and 3,696,191 all incorporated herein by reference. An enzyme of a mixture of several compatible enzymes in the current invention constitutes 0.002% to 2.0% in one embodiment or 0.05% to 1.5% in another embodiment or in yet another embodiment 0.1% to 0.5%.

Water may also be present in the oral compositions of the invention. Water, employed in the preparation of commercial oral compositions should be deionized and free of organic impurities. Water commonly makes up the balance of the compositions and includes 10% to 90%, 20% to 60% or 10% to 30% by weight of the oral compositions. This amount of water includes the free water which is added plus that amount which is introduced with other materials such as with sorbitol or any components of the invention.

Compositions of the present invention may also comprise a humectant, e.g., to prevent the composition from hardening upon exposure to air. Certain humectants can also impart desirable sweetness or flavor to dentifrice compositions. The humectant, on a pure humectant basis, generally includes 15% to 70% in one embodiment or 30% to 65% in another embodiment by weight of the dentifrice composition. Suitable humectants include edible polyhydric alcohols such as glycerine, sorbitol, xylitol, propylene glycol as well as other polyols and mixtures of these humectants. Mixtures of glycerine and sorbitol may be used in certain embodiments as the humectant component of the toothpaste compositions herein.

The compositions of the present invention may also include one or more antibacterial agents. Antibacterial agents are known in the art, and include benzoic acid, sodium benzoate, potassium benzoate, boric acid, and phenolic compounds such as betanaphthol, chlorothymol, thymol, anethole, eucalyptol, carvacrol, menthol, phenol, amylphenol, hexylphenol, heptylphenol, octylphenol, hexylresorcinol, laurylpyridinium chloride, myristylpyridinium chloride, cetylpyridinium fluoride, cetylpyridinium chloride, cetylpyridinium bromide, and halogenated diphenyl ethers, such as triclosan. Compositions of the present invention may also include one or more basic amino acids, e.g., arginine, in free base or salt form. Such agents may be added in effective amounts, e.g., from 1% to 20% by weight based on the total weight of the composition, depending on the agent chosen.

The compositions of the present invention may incorporate one or more antisensitivity agents, e.g., potassium salts such as potassium nitrate, potassium bicarbonate, potassium chloride, potassium citrate, and potassium oxalate; capsaicin; eugenol; strontium salts; zinc salts; chloride salts and combinations thereof. Such agents may be added in effective amounts, e.g., from 1% to 20% by weight based on the total weight of the composition, depending on the agent chosen. The compositions of the present invention may also be used to treat hypersensitivity by blocking dentin tubules when applied to a tooth.

The compositions of the present invention may also include a tooth whitening or tooth bleaching composition, which are known in the art. Suitable whitening and bleaching composition include peroxides, metal chlorites, persulfates. Peroxides include hydroperoxides, hydrogen peroxide, peroxides of alkali and alkaline earth metals, organic peroxy compounds, peroxy acids, and mixtures thereof. Peroxides of alkali and alkaline earth metals include lithium peroxide, potassium peroxide, sodium peroxide, magnesium peroxide, calcium peroxide, barium peroxide, and mixtures thereof. Other peroxides include perborate, urea peroxide, and mixtures thereof. Suitable metal chlorites may include calcium chlorite, barium chlorite, magnesium chlorite, lithium chlorite, sodium chlorite, and potassium chlorite. Such agents may be added in effective amounts, e.g., from 1% to 20% by weight based on the total weight of the composition, depending on the agent chosen.

In addition to the above described components, the embodiments of this invention can contain a variety of optional dentifrice ingredients some of which are described below. Optional ingredients include, for example, but are not limited to, adhesives, sudsing agents, flavoring agents, sweetening agents, additional antiplaque agents, abrasives, and coloring agents. These and other optional components are further described in U.S. Pat. No. 5,004,597, to Majeti; U.S. Pat. No. 3,959,458 to Agricola et al. and U.S. Pat. No. 3,937,807, to Haefele.

Abrasive selection for the present oral compositions may account for the abrasive type, fineness (particle size), particle size distribution and amount of abrasive, to ensure that tooth enamel is not excessively abraded during normal use of the composition, but is sufficiently cleaned and/or polished. In the context of oral care, the efficacy of the abrasive can be expressed based on a cleaning or an abrasion basis for a dentifrice, namely the pellicle cleaning ratio (PCR) or the radioactive dentin abrasion (RDA) respectively. Methods of performing PCR and RDA are well known in the art, e.g., described in e.g., U.S. Pat. Nos. 5,939,051 and 6,290,933.

In certain embodiments, the composition is safe for oral use with humans or other animals, and any orally or cosmetically acceptable abrasive fulfilling the requirements set forth above can be selected for an oral composition.

Additional abrasives may also be included in the compositions of the present invention, include alumina (including calcined aluminum oxide), diatomaceous earth, pumice, calcium carbonate, cuttlebone, insoluble phosphates, composite resins, such as melamine resin, phenolic resin, and urea-formaldehyde resin, polycarbonate, boron carbide, microcrystalline wax, microcrystalline cellulose, including combinations of colloidal microcrystalline cellulose and carboxymethylcellulose, and combinations and derivatives thereof. Among insoluble phosphates useful as abrasives are orthophosphates, polymetaphosphates and pyrophosphates. Illustrative examples are dicalcium orthophosphate dihydrate, dicalcium phosphate dihydrate, calcium hydrogen phosphate, calcium pyrophosphate, β-calcium pyrophosphate, tricalcium phosphate, calcium metaphosphate, potassium metaphosphate, and sodium metaphosphate.

In certain embodiments, the oral composition is in the form of a dentifrice, and the exemplary carrier is substantially semi-solid or solid. The carrier can be aqueous, i.e., comprising 5% to 95% water. In other embodiments, the carrier is substantially non-aqueous. The carrier optionally comprises, for example, oral care active ingredients, surface active agents, such as surfactants, emulsifiers, and foam modulators, viscosity modifiers and thickeners, humectants, diluents, fillers, additional pH modifying agents, colorants, preservatives, solvents, and combinations thereof. It is understood that while general attributes of each of the above categories of materials may differ; there may be some common attributes and any given material may serve multiple purposes within two or more of such categories of materials. As recognized by one of skill in the art, the oral compositions optionally include other materials in addition to those components previously described, including for example, emollients, moisturizers, mouth feel agents and the like. Examples of suitable carriers for oral compositions are discussed in U.S. Pat. No. 6,669,929 to Boyd et al., U.S. Pat. No. 6,379,654 to Gebreselassie et al., and U.S. Pat. No. 4,894,220 to Nabi et al.

The oral composition optionally comprises an anti-calculus composition, such as, for example, one or more of the anti-calculus compositions discussed in U.S. Pat. No. 5,292,526 to Gaffar, et al. In various embodiments, the anti-calculus composition includes one or more polyphosphates. The anti-calculus composition can include at least one wholly or partially neutralized alkali metal or ammonium tripolyphosphate or hexametaphosphate salt present in the oral composition at an effective anti-calculus amount. The anti-calculus active can also include at least one water soluble, linear, molecularly dehydrated polyphosphate salt effective in an anticalculus amount. The anti-calculus active can also include a mixture of potassium and sodium salts, at least one of which is present in an effective anti-calculus amount as a polyphosphate anti-calculus agent. The anti-calculus active agent can also contain an effective anticalculus amount of linear molecularly dehydrated polyphosphate salt anti-calculus agent present in a mixture of sodium and potassium salts. The ratio of potassium to sodium in the composition can be up to less than 3:1. The polyphosphate can be present in the oral composition in various amounts, such as an amount wherein the weight ratio of polyphosphate ion to anti-bacterial agent ranges from in excess of 0.72:1 to less than 4:1, or wherein the weight ratio of the anti-bacterial enhancing agent to the polyphosphate ion ranges from 1:6 to 2.7:1, or wherein the weight ratio of the anti-bacterial enhancing agent to the polyphosphate ranges from 1:6 to 2.7:1. Other useful anticalculus agents include polycarboxylate polymers and polyvinyl methyl ether/maleic anhydride (PVM/MA) copolymers, such as GANTREZ®.

Another active agent useful in dentifrice compositions of the present invention are antibacterial agents, which may be present in amounts of 0.001 to 3.0% by weight of the oral composition. A non-limiting list of useful additional oral care compounds includes non-ionic antibacterial agents, including phenolic and bisphenolic compounds, such as, halogenated diphenyl ethers, including triclosan (2,4,4'-trichloro-2'-hydroxy-diphenylether, triclocarban (3,4,4-trichlorocarbanilide), as well as 2-phenoxyethanol, benzoate esters, and carbanilides. A halogenated diphenyl ether, such as triclosan, can be present in an amount of 0.3% by weight of the oral composition, for example.

Suitable surface active agents are those that are reasonably stable throughout a wide pH range. These compounds are well known in the art, and include non-soap anionic (e.g., sodium lauryl sulfate (SLS), N-myristoyl, and N-palmitoyl sarcosine), nonionic (e.g., Polysorbate 20 (polyoxyethylene 20 sorbitan monolaurate, TWEEN® 20) and Polysorbate 80 (polyoxyethylene 20 sorbitan mono-oleate, TWEEN® 80), Poloxamer 407, available under the trade name PLURONIC® F127 from BASF Corporation), cationic, zwitterionic (e.g., cocamidopropyl betaine and lauramido propyl betaine), and amphoteric organic synthetic detergents. Examples of suitable surface active agents for use in oral compositions are discussed in, for example, U.S. Pat. No. 4,894,220 to Nabi et al., U.S. Pat. No. 6,555,094 to Glandorf et al., and U.S. Pat. No. 6,706,256 to Lawlor. In various embodiments, one or more surface active agents are present in the oral composition of the present invention in the range of 0.001% to 5%, or 0.5% to 2.5%.

Optional thickeners for use in oral compositions include natural and synthetic gums and colloids, such as carrageenan (Irish moss), xanthan gum, sodium carboxymethyl cellulose, starch, polyvinylpyrrolidone, hydroxyethylpropyl cellulose, hydroxybutyl methyl cellulose, hydroxypropylmethyl cellulose, and hydroxyethyl cellulose. In various embodiments, the thickening agent is present in the dentifrice composition in amounts of 0.1 to 10% by weight, or 0.5 to 4% by weight.

The orally-acceptable dentifrice carrier vehicle used to prepare the dentifrice composition optionally comprises a humectant. The humectant can be glycerin, sorbitol, and xylitol, propylene glycol of molecular weight in the range of 200 to 1,000; or other humectants and mixtures thereof. The humectant concentration typically totals 5 to 70% by weight of the oral composition. Water is typically present in an amount of at least 10% by weight, and generally 25 to 70% by weight of the oral composition.

Synthetic anionic linear polycarboxylates are efficacy enhancing agents for optional use in oral compositions having certain active ingredients, including antibacterial, anti-tartar or other active agents within the oral composition. Such anionic polycarboxylates are generally employed in the form of their free acids, or partially or fully neutralized water soluble alkali metal (e.g., potassium and preferably sodium) or ammonium salts. The terms "synthetic" and "linear" exclude known thickening or gelling agents comprising carboxymethylcellulose and other derivatives of cellulose and natural gums, nor carbopols having reduced solubility due to cross-linkages.

Preferred copolymers are 1:4 to 4:1 copolymers of maleic anhydride or acid with another polymerizable ethylenically unsaturated monomer, preferably methyl vinyl ether (methoxyethylene) having a molecular weight (M.W.) of 30,000 to 1,000,000. One useful copolymer is methylvinylether/maleic anhydride. Examples of these copolymers are available from ISP Corporation under the trade name GANTREZ®, When present, the anionic polycarboxylate is employed in amounts effective to achieve the desired enhancement of the efficacy of any antibacterial, antitartar or other active agent within the dentifrice composition. In various embodiments, a synthetic anionic polycarboxylate is included in the oral composition is present at 0.001 to 5%, or 0.1 to 2.0% of the oral composition.

The oral composition of the present invention can be made by any of the methods known in the art for combining ingredients to make oral care compositions. Examples of methods that can be used are set forth in, e.g., U.S. Pat. No. 6,403,059 to Martin et al.; Clinical Pharmacology for Dental Professionals (Mosby-Year Book, Inc., 3rd ed. 1989); Mosby's Dental Hygiene: Concepts, Cases and Competencies, (Daniel, S. and Harfst, S. eds., Elsevier Science Health Science Div. 2002); and Ernest W. Flick, Cosmetic and Toiletry Formulations, 2nd ed.

The present invention provides for methods and processes of using the oral compositions of the present invention to clean and/or polish oral surfaces. Further, the oral compositions optionally treat and inhibit oral conditions, such as oral inflammatory conditions, dental plaque, and dental calculus. The oral compositions can be applied to the subject in any suitable manner known in the art; for example, by introducing the oral composition to the subject's oral cavity using a suitable applicator or delivery device, such as a brush, dental strip, film, syringe, tape, pill, or any other applicator or delivery device known in the art. The compositions can be used in prophylactic methods and processes to promote and maintain oral health, appearance, maintain systemic health and the like. The oral compositions can be repeatedly applied to the subject over a number of days according to a particular treatment schedule to treat and/or inhibit stain, plaque, calculus or tartar formation. Instructions setting forth the treatment schedule can be provided in commercial packaging with the product, as commercially prepared and stored.

Without intending to be bound by theory, it is believed that the silica abrasives utilized in the oral compositions of the present invention have an initial average particle size. When the oral compositions of the present invention are used to brush soft tissues, e.g., to remove plaque or pellicle, the silica abrasives are sufficient to remove such soft tissue, e.g., from tooth surfaces. Thus, the oral compositions initially have a high PCR. However, as the silica abrasive particles are contacted against hard dental surfaces, e.g., dentin or enamel, they fracture into smaller particles; thereby resulting in a low RDA. Accordingly, soft tissue has been ablated, and hard tissues are protected from abrasion when the compositions of the present invention are used to treat the oral cavity. It is believed that as the composition is used in the mouth, the PCR and/or RDA may both decrease in value over time due to the reduction in silica abrasive size.

The resulting fragmented silica particles resulting from contact with hard surfaces also impart additional unexpected benefits; namely, the ability to polish tooth surfaces and/or plug dental tubules, resulting in cleaner teeth and/or reduced tooth sensitivity. Accordingly, the compositions of the present invention result in the improved cleaning, polishing, and reduction of sensitivity of teeth.

The present invention is further illustrated through the following non-limiting example(s).

EXAMPLE 1

Characteristics of Silica A and Silica B are determined as follows. Silica A Is Grace VP5. Silica B is ZEODENT® 105 from J. M. Huber (Havre de Grace, Md., USA).

Conditions used for Einlehner testing were 174000 revolutions in 120 min using a brass screen and 100 g of silica in 1000 mL. Oil absorption and mean particle size were measured by methods known by those of skill in the art. Measurements are presented in Table 1.

TABLE 1

|  | Silica A | Silica B |
| --- | --- | --- |
| Oil absorption (cc/100 g) | 80-100 | 50-65 |
| Mean particle size (μm) | 9-13 | 8-12 |
| $d_{10}$ (μm)* | 2.74 | 2.58 |
| Brass Einlehner hardness | 6-9 | 12-18 |

*The term "d" refers to the upper limit of a particle size; thus, the term $d_{10}$ indicates that 10% o particles have a size smaller than the value of $d_{10}$.

A 20% w/w slurry is prepared with Silicas A and B using deionized water. The particle size distribution of the initial slurry is determined with a Malvern 2000 particle size analyzer with Hydro 2000S Small Volume Automated Sample Dispersion Unit. The slurry is sonicated in a water bath before measurement for 1 minute to break up any large agglomerates. Using a flatbed cross brushing machine, 20 ml of slurry are added to an aluminum trough measuring ½"×3½" with a sidewall of 70°. A soft, square head bristle brush (Head dimensions approximately L×W 2.8 cm×1.0 cm) is mounted to move along the entire base of the aluminum trough. Weight is added on the back of the brush head (250 grams) to produce a normal force during brushing. The brushing machine is run at a rate of 100 double strokes per minute along the aluminum surface for a total of 300 strokes. Following brushing, the slurry is removed from the base of the trough, and sonicated for 1 minute. Samples are loaded into the Malvern 2000 particle sizing analyzer. The silica abrasive particle sizes are then determined, and are presented in table 2.

TABLE 2

|  | Silica A | Silica B |
| --- | --- | --- |
| % reduction in mean particle size | 18.5% | 0.7% |
| $d_{10}$ after procedure (μm) | 2.45 | 2.55 |
| % reduction in $d_{10}$ | 10.6% | 1.2% |

Surprisingly, the results will indicate the ability of Silica A to break down significantly during a brushing regimen, while Silica 13 remains relatively unchanged.

EXAMPLE 2

The PCR and RDA values of various Silica A slurries are determined by methods as previously described herein. 10%, 15%, 20% and 30% w/w silica slurries are prepared, and their PCR and RDA values are determined by methods as previously described herein. Results are presented in Table 3.

TABLE 3

|  | 10% VP5 | 15% VP5 | 20% VP5 | 30% VP5 |
| --- | --- | --- | --- | --- |
| PCR | 72 | 76 | 84 | 86 |
| RDA | 83 | 95 | 93 | 112 |
| PCR/RDA ratio | 0.86 | 0.80 | 0.90 | 0.77 |

EXAMPLE 3

Dentifrice compositions, e.g, toothpastes are prepared in accordance with Table 4.

TABLE 4

|  | MF-A | MF-B | WD-A | WD-B |
| --- | --- | --- | --- | --- |
| Silica A | 22.8 |  | 21.9 |  |
| Silica B |  | 22.8 |  | 21.9 |
| Sorbitol | 40.2 | 40.2 | 13.6 | 13.6 |
| Water | 29 | 29 | 37.1 | 37.1 |
| PEG | 3 | 3 |  |  |
| SLS | 1.5 | 1.5 | 1.5 | 1.5 |
| Cellulose gum | 0.6 | 0.6 | 0.8 | 0.8 |
| Sodium pyrophosphate | 0.5 | 0.5 |  |  |
| Cocamidopropyl betaine | 0.4 | 0.4 |  |  |
| Triclosan |  |  | 0.3 | 0.3 |
| Sodium sulfate | 0.3 | 0.3 | 0.1 | 0.1 |
| Glycerin |  |  | 19.9 | 19.9 |
| Titanium dioxide |  |  | 0.1 | 0.1 |
| Sodium fluoride | 0.2 | 0.2 | 0.3 | 0.3 |
| PVMA/MA copolymer |  |  | 2 | 2 |
| Carrageenan |  |  | 0.3 | 0.3 |
| Flavor and color | 1.5 | 1.5 | 2.1 | 2.1 |

EXAMPLE 4

Two groups of 30 people suffering from dental sensitivity are given either tooth paste MF-A or MF-B, and are instructed use the compositions as their sole dentifrice for one month in accordance with their normal brushing practices. At the end of one month, 75% of people brushing with MF-A report a reduction tooth sensitivity, and 10% of people brushing with MF-B report a reduction in tooth sensitivity. At the end of one month, 3% of people brushing with MF-A report increased tooth sensitivity, and 15% of people brushing with MF-B report increased tooth sensitivity.

EXAMPLE 5

Two groups of 50 people are given either toothpaste WD-A or WD-B, and are instructed to use the compositions as their sole toothpaste for one month in accordance with their normal brushing practices. 80% of people brushing with WD-A report that they observed a whitening/polishing effect, whereas 5% of people brushing with WD-B report that they observed a whitening/polishing effect.

EXAMPLE 6

Two groups of 15 smokers (average 1.4 packs per day) are given either toothpaste MF-A or MF-B, and are instructed to use the composition as their sole toothpaste in accordance with their normal brushing practices. At the end of one month, 85% of people brushing with MF-A perceived that staining of their teeth decreased, and 12% of people brushing with MF-B perceived that their tooth stains decreased.

EXAMPLE 7

The RDA and PCR of two compositions comprising 20% Silica A and 20% Silica B are determined by methods a previously described herein. The two compositions are essentially identical, with the exception of the different silica abrasives. Results are presented in Table 5

TABLE 5

|  | 20% Silica A | 20% Silica B |
| --- | --- | --- |
| RDA | 112 | 207 |
| PCR | 93 | 103 |
| PCR/RDA | 0.83 | 0.5 |

We claim:

1. An oral composition comprising an orally-acceptable carrier and an abrasive system consisting essentially of a precipitated silica abrasive, wherein
    the precipitated silica abrasive has an average particle size of from 9 μm to 13 μm; and
    an Einlehner hardness of from 6 to 9;
    wherein the mean particle size of the precipitated silica abrasive is reduced by 16% to 20% after being applied to a hard surface in an oral cavity for from 30 seconds to 5 minutes;
    wherein the precipitated silica abrasive is present in an amount from 10% to 20% weight of the composition;
    wherein the precipitated silica abrasive has an oil absorption from 80 cc/100 g to 100 cc/100 g;
    wherein the composition has a pellicle cleaning ratio of from 80 to 105 and has a radioactive dentin abrasion of less than 150;
    wherein a 10% aqueous slurry consisting of the precipitated silica abrasive has a PCR/RDA ratio of from 0.7 to 0.9; and
    wherein the only silica in the oral composition is the precipitated silica.

2. The composition according to claim 1 wherein the precipitated silica abrasive has a $d_{10}$ of from 2.5 μm to 2.9 μm.

3. The composition according to claim 1, further comprising at least one surfactant selected from sodium lauryl sulfate, cocamidopropyl betaine, and combinations thereof.

4. The composition according to claim 3, further comprising at least one humectant selected from glycerin, sorbitol and combinations thereof.

5. The composition according to claim 4, further comprising at least one polymer selected from polyethylene glycols, polyvinylmethyl ether maleic acid copolymers, polysaccharides, and combinations thereof.

6. The composition according to claim 1, further comprising a tooth desensitizing agent.

7. The composition according to claim 1, further comprising a tooth whitening compound.

8. The composition according to claim 1 which is a toothpaste or gel.

9. The composition according to claim 1 wherein the RDA of the oral composition after it has been applied to a hard surface in the oral cavity for five seconds is from 1.2 to 1.6 times greater than the RDA of the same composition after it has been applied to a hard surface in the oral cavity for from 30 seconds to 5 minutes.

10. The composition according to claim 1, wherein a 10% aqueous slurry consisting of the precipitated silica abrasive has a PCR of from 65 to 80.

11. The composition according to claim 1, wherein a 10% aqueous slurry consisting of the precipitated silica abrasive has a RDA of from 75 to 91.

12. The oral composition according to claim 1, further comprising
- at least one surfactant selected from sodium lauryl sulfate, cocamidopropyl betaine, and combinations thereof;
- at least one humectant selected from glycerin, sorbitol and combinations thereof; and
- at least one polymer selected from polyethylene glycols, polyvinylmethyl ether maleic acid copolymers, polysaccharides, and combinations thereof.

13. The composition of claim 12, wherein the RDA of the oral composition after it has been applied to a hard surface in the oral cavity for five seconds is from 1.3 to 1.6 times greater than the RDA of the oral composition after it has been applied to a hard surface in the oral cavity for from 1 minute to 5 minutes.

* * * * *